(12) United States Patent
Johnson et al.

(10) Patent No.: US 6,770,771 B2
(45) Date of Patent: Aug. 3, 2004

(54) POLYMERIZATION OF OLEFINS

(75) Inventors: Lynda Kaye Johnson, Wilmington, DE (US); Lissa Taka Jennings Nelson, Highland Park, IL (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/131,743

(22) Filed: Apr. 24, 2002

(65) Prior Publication Data

US 2002/0156212 A1 Oct. 24, 2002

Related U.S. Application Data

(62) Division of application No. 09/362,432, filed on Jul. 28, 1999, now Pat. No. 6,403,738.
(60) Provisional application No. 60/094,502, filed on Jul. 29, 1998.

(51) Int. Cl.$^7$ .............................. C08F 4/44; C08F 10/02
(52) U.S. Cl. .............................. 556/20; 556/51; 556/57; 556/137; 556/138; 502/162; 502/167; 502/168; 526/161; 526/171; 526/172
(58) Field of Search .................................. 526/171, 161, 526/172; 556/20, 51, 57, 137, 138; 502/162, 167, 168

(56) References Cited

U.S. PATENT DOCUMENTS

| 5,714,556 A | 2/1998 | Johnson et al. | 526/135 |
|---|---|---|---|
| 5,880,241 A | 3/1999 | Brookhart et al. | 526/348 |
| 6,103,658 A | * 8/2000 | Mackenzie et al. | 502/167 |

FOREIGN PATENT DOCUMENTS

| WO | WO 96/23010 | 8/1996 | C08F/210/16 |
|---|---|---|---|
| WO | WO 98/40374 | 9/1998 | C07D/319/02 |
| WO | WO 98/40420 | 9/1998 | C08F/10/00 |
| WO | WO 98/47933 | 10/1998 | C08F/10/00 |

OTHER PUBLICATIONS

M. Doring, et al., Nitrogen Derivates of Oxalic Acid as New Complexing Agents, *Z. anorg. allg. Chem.*, 620, 551–560, 1994.

Lynda Kaye Johnson, et al., New Pd(II)– and Ni(II)–Based Catalysts for Polymerization of Ethylene and Alpha–Olefins, *J. Am. Chem. Soc.*, 117, 6414–6415, 1995.

D. Lindauer, et al., Aminolysis of Bis–Imodyl Chlorides of Oxalic Acid—I. Conversions and Aromatic and Aliphatic Amines, *J. Prakt. Chem.*, 337, 143–152, 1995.

Lynda Kaye Johnson, et al., Copolymerization of Ethylene and Propylene with Functionalized Vinyl Monomers by Palladium (II) Catalysts, *J. Am. Chem. Soc.*, 118, 267–268, 1996.

D. Lindauer, et al., Aminolysis of Bis–Imodyl Chlorides of Oxalic Acid –I. Conversions with Aromatic and Aliphatic Amines, *J. Prakt. Chem.*, 337, 143–152, 1995.

Stefan Mecking, et al., Mechanistic Studies of the Palladium–Catalyzed Copolymerization of Ethylene and Alpha––Olefins with methyl Acrylate, *J. Am. Chem. Soc.*, 120, 888–889, 1998.

C. L. Arora, et al., Carbaryl metal chloride complexes and their persistence, *Chemical Abstracts*, 121, No. 20, Nov. 14, 1994.

C. L. Arora, et al., Carbaryl metal chloride complexes and their persistence, *Asian Journal of Chemistry*, 6, No. 3, 676–677, 1994.

Daniel D. VanderLende, et al., Monomeric Nickel(II) Amido Complexes. Synthesis, Reactivity, and Dynamics, *Inorg. Chem.*, 34, 5319–5326, 1995.

Allen L. Seligson, et al., Alkyl and Hydrido Phenoxo Complexes of Nickel(II), Palladium(II), and Platinum(II). Hydrido Amido Complexes of Palladium, *Inorg. Chem.*, 30, 3371–3381, 1991.

Mueller, Eugene et al., Imidazole Derivatives by the Action of Oxygen on Lithium Aldimines, *Chem.–ZTG.*, 96, 529, 1972.

Bauer, Rudolph, On Oxalic Acid Imide Chlorides, *Berichte d.D. Chem. Gesellschaft*, 2650–2662, 1907.

* cited by examiner

Primary Examiner—Robert Deshon Harlan

(57) ABSTRACT

Various olefins may be polymerized using a catalyst systems containing selected α-diimine, urethane or urea ligands, some of them novel, complexed to nickel, palladium or other selected transition metals. The polymers are useful as molding resins and elastomers.

8 Claims, No Drawings

POLYMERIZATION OF OLEFINS

This application is a divisional of application Ser. No. 09/366,432 filed on Jul. 28, 1999 now U.S. Pat. No. 6,403,738 which claims benefit of provisional application No. 60/094,502 filed Jul. 29, 1998.

FIELD OF THE INVENTION

Various nickel and palladium complexes, for example of α-diimines substituted at the carbon atoms by heteroatoms such as nitrogen or oxygen, and selected ureas and urethanes, may be used as polymerization catalysts for olefins such as ethylene. The palladium catalysts also polymerize polar comonomers.

TECHNICAL BACKGROUND

Recently polymerization catalysts containing late transition metals such as palladium and nickel have been reported. Among these compounds are complexes of α-diimines (see World Patent Application 96/23010) and various other types of ligands (see U.S. Pat. No. 5,714,556). These catalysts can, under various conditions, make unique polyolefins, such as those that contain "abnormal" branching patterns when compared to polymers made by the well known Ziegler-Natta- and metallocene-type catalysts. In addition some of these catalysts can polymerize olefins which are often not polymerizable with most catalysts based on transition metal compounds, for example polar olefins such as olefinic esters. Therefore, new olefin polymerization catalysts containing late transition metals are of great interest.

The use of palladium containing catalysts to polymerize olefins is described in S. Mecking, et al., J. Am. Chem. Soc., vol. 120, p. 888–899 (1998). Nickel diimine complexes as olefin polymerization catalysts are described in L. K. Johnson, et al., J. Am. Chem. Soc., vol. 117, p. 6414–6415 (1995), and L. K. Johnson, et al., J. Am. Chem. Soc., vol. 118, p.267–268 (1996). None of the catalysts described herein are described in these papers.

Certain iron, cobalt and molybdenum complexes of α-diimines having nitrogen substituted in the backbone are described in M. Doring, et al., Z. Anorg. Allg. Chem., vol. 620, p. 551–560 (1994). None of these substituted α-diimines or these metal complexes are claimed herein.

The reactions of various bis(imidoyl chlorides) of oxalic acid with amines, diamines and aminoalcohols to form various nitrogen and oxygen substituted α-diimines is described in D. Lauder, et al., J. Prakt. Chem., vol. 337, p. 143–152 and ibid., p. 508–515 (1995). None of the substituted α-diimines enumerated in these papers is claimed herein.

SUMMARY OF THE INVENTION

This invention concerns a first process for the polymerization of one or more olefins of the formula $H_2C{=}CHR^1$ and optionally one or more olefins of the formula $H_2C{=}CHR^2$, comprising, contacting said olefins with a complex containing a transition metal selected from the group consisting of palladium, nickel, titanium, zirconium, scandium, vanadium, chromium, iron, cobalt, and a rare earth metal and a ligand of the formula

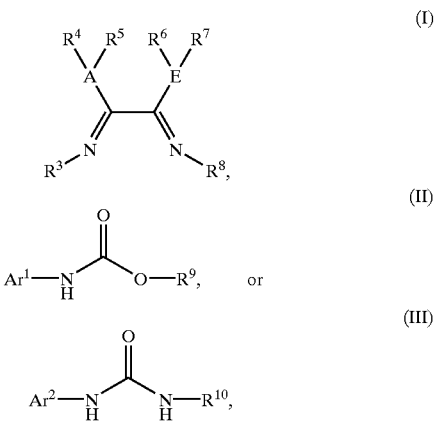

which is an active polymerization catalyst, wherein:
  each $R^1$ is independently hydrogen or alkyl;
  each $R^2$ is independently substituted alkyl or $-CO_2R^{50}$;
  A and E are each independently oxygen, sulfur, phosphorous or nitrogen;
  $R^3$ and $R^8$ are each independently hydrocarbyl or substituted hydrocarbyl provided that the carbon atom bound to the nitrogen atom is bound to at least two other carbon atoms;
  $R^4$, $R^5$, $R^6$ and $R^7$ are each independently hydrocarbyl or substituted hydrocarbyl;
  $Ar^1$ and $Ar^2$ are each independently aryl or substituted aryl;
  $R^9$ and $R^{10}$ are each independently hydrocarbyl or substituted hydrocarbyl;
  $R^{50}$ is hydrocarbyl or substituted hydrocarbyl;
  and provided that:
    when said ligand is (II) or (III) said transition metal is nickel;
    when $H_2C{=}CHR^2$ is present a palladium complex is present;
    the members of any one or more of the pairs $R^4$ and $R^5$, $R^6$ and $R^7$, $R^4$ and $R^6$, and $R^5$ and $R^7$ taken together may form a ring;
    when A is oxygen or sulfur, $R^5$ is not present; and
    when E is oxygen or sulfur, $R^7$ is not present.

This invention also concerns a second process for the polymerization of one or more olefins of the formula $H_2C{=}CHR^1$ and optionally one or more olefins of the formula $H_2C{=}CHR^2$, comprising, contacting said olefins, a first compound of the formula

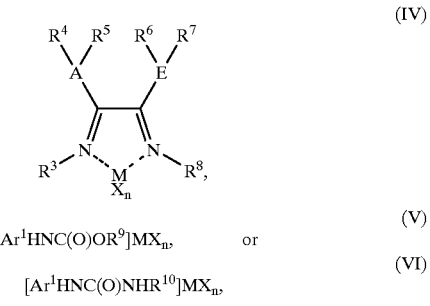

and:
  (a) a second compound W, which is a neutral Lewis acid capable of abstracting $X^-$ from M to form $WX^-$, and which is also capable of transferring an alkyl group or a hydride to M, provided that WX⁻ is a weakly coordinating anion; or (b) a combination of a third compound which is capable of transferring an alkyl or hydride group to M and a fourth compound which is a neutral Lewis acid which is capable of abstracting X⁻, a hydride or an alkyl group from M to form a weakly coordinating anion; or (c) when at least one of X is a hydride or alkyl group, a fifth compound which is a cationic Lewis or Bronsted acid whose counterion is a weakly coordinating anion;

wherein:
M is Ni, Pd, Ti, Zr, Sc, V, Cr, Fe, Co or a rare earth metal;
each X is independently a monoanion;
n is equal to the oxidation number of M;
each $R^1$ is independently hydrogen or alkyl;
each $R^2$ is independently substituted alkyl or —$CO_2R^{50}$;
A and E are each independently oxygen, sulfur, phosphorous, or nitrogen;
$R^3$ and $R^8$ are each independently hydrocarbyl or substituted hydrocarbyl provided that the carbon atom bound to the nitrogen atom is bound to at least two other carbon atoms;
$R^4$, $R^5$, $R^6$ and $R^7$ are each independently hydrocarbyl or substituted hydrocarbyl;
$Ar^1$ and $Ar^2$ are each independently aryl or substituted aryl;
$R^9$ and $R^{10}$ are each independently hydrocarbyl or substituted hydrocarbyl;
$R^{50}$ is hydrocarbyl or substituted hydrocarbyl;

and provided that
when said first compound is (II) or (III), M is Ni;
the members of any one or more of the pairs $R^4$ and $R^5$, $R^6$ and $R^7$, $R^4$ and $R^6$, and $R^5$ and $R^7$ taken together may form a ring;
when $H_2C=CHR^2$ is present a palladium complex is present;
when A is oxygen or sulfur, $R^5$ is not present; and
when E is oxygen or sulfur, $R^7$ is not present.

This invention also includes a compound of the formula

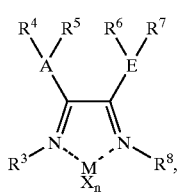

(IV)

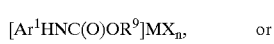

(V)

(VI)

wherein:
M is Ni, Pd, Ti, Zr, Sc, V, Cr, Fe, Co or a rare earth metal;
each X is independently a monoanion;
n is equal to the oxidation number of M;
A and E are each independently oxygen, sulfur, phosphorous, or nitrogen;
$R^3$ and $R^8$ are each independently hydrocarbyl or substituted hydrocarbyl provided that the carbon atom bound to the nitrogen atom is bound to at least two other carbon atoms;

$R^4$, $R^5$, $R^6$ and $R^7$ are each independently hydrocarbyl or substituted hydrocarbyl;
$Ar^1$ and $Ar^2$ are each independently aryl or substituted aryl;
$R^9$ and $R^{10}$ are each independently hydrocarbyl or substituted hydrocarbyl;

and provided that
when said compound is (V) or (VI), M is Ni;
the members of any one or more of the pairs $R^4$ and $R^5$, $R^6$ and $R^7$, $R^4$ and $R^6$, and $R^5$ and $R^7$ taken together may form a ring;
when A is oxygen or sulfur, $R^5$ is not present; and
when E is oxygen or sulfur, $R^7$ is not present.

Also disclosed herein is a compound of the formula

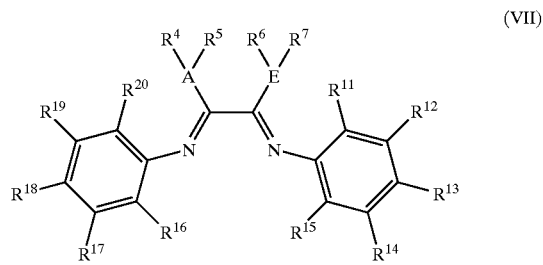

(VII)

wherein:
A and E are each independently oxygen, sulfur, phosphorous, or nitrogen;
$R^4$, $R^5$, $R^6$ and $R^7$ are each independently hydrocarbyl or substituted hydrocarbyl;
$R^{11}$ is hydrocarbyl or substituted hydrocarbyl containing 2 or more carbon atoms, or a functional group;
$R^{12}$, $R^{13}$, $R^{14}$, $R^{15}$, $R^{16}$, $R^{17}$, $R^{18}$, $R^{19}$, and $R^{20}$ are each independently hydrogen, hydrocarbyl, substituted hydrocarbyl or a functional group;

and provided that
the members of any one or more of the pairs $R^4$ and $R^5$, $R^6$ and $R^7$, $R^4$ and $R^6$, and $R^5$ and $R^7$ taken together may form a ring;
any two of $R^{11}$, $R^{12}$, $R^{13}$, $R^{14}$, $R^{15}$, $R^{16}$, $R^{17}$, $R^{18}$, $R^{19}$, and $R^{20}$ vicinal to one another taken together may form a ring with the further proviso that if $R^{11}$ and $R^{12}$ are taken together to form a ring, then $R^{11}$ and $R^{12}$ taken together contain at least 2 carbon atoms;
when A is oxygen or sulfur, $R^5$ is not present; and
when E is oxygen or sulfur, $R^7$ is not present.

DETAILS OF THE INVENTION

Herein, certain terms are used. Some of them are:

A "hydrocarbyl group" is a univalent group containing only carbon and hydrogen. If not otherwise stated, it is preferred that hydrocarbyl groups (and alkyl groups) herein contain 1 to about 30 carbon atoms.

By "substituted hydrocarbyl" herein is meant a hydrocarbyl group which contains one or more substituent groups which are inert under the process conditions to which the compound containing these groups is subjected. The substituent groups also do not substantially interfere with the process. If not otherwise stated, it is preferred that substituted hydrocarbyl groups herein contain 1 to about 30 carbon atoms. Included in the meaning of "substituted" are heteroaromatic rings.

By "(inert) functional group" herein is meant a group other than hydrocarbyl or substituted hydrocarbyl which is inert under the process conditions to which the compound containing the group is subjected. The functional groups also do not substantially interfere with any process described herein that the compound in which they are present may take part. Examples of functional groups include halo (fluoro, chloro, bromo and iodo), trialkylsilyl, ether such as —OR$^{22}$ wherein R$^{22}$ is hydrocarbyl or substituted hydrocarbyl. In cases in which the functional group may be near a nickel or palladium atom the functional group should not coordinate to the metal atom more strongly than the groups in those compounds are shown as coordinating to the metal atom, that is they should not displace the desired coordinating group.

By an "alkyl aluminum compound" is meant a compound in which at least one alkyl group is bound to an aluminum atom. Other groups such as alkoxide, hydride, and halogen may also be bound to aluminum atoms in the compound.

By "neutral Lewis base" is meant a compound, which is not an ion, which can act as a Lewis base. Examples of such compounds include ethers, amines, sulfides, and organic nitriles.

By "cationic Lewis acid" is meant a cation which can act as a Lewis acid. Examples of such cations are sodium and silver cations.

By relatively noncoordinating (or weakly coordinating) anions are meant those anions as are generally referred to in the art in this manner, and the coordinating ability of such anions is known and has been discussed in the literature, see for instance W. Beck., et al., Chem. Rev., vol. 88 p. 1405–1421 (1988), and S. H. Strauss, Chem. Rev., vol. 93, p. 927–942 (1993), both of which are hereby included by reference. Among such anions are those formed from the aluminum compounds mentioned previously and X$^-$, including R$^{33}_3$AlX$^-$, R$^{33}_2$AlClX$^-$, R$^{33}$AlCl$_2$X$^-$, and "R$^{33}$AlOX$^-$", wherein R$^{33}$ is alkyl. Other useful noncoordinating anions include BAF$^-$ {BAF=tetrakis[3,5-bis(trifluoromethyl) phenyl]borate}, SbF$_6^-$, PF$_6^-$, and BF$_4^-$, trifluoromethanesulfonate, p-toluenesulfonate, (R$_f$SO$_2$)$_2$ N$^-$, and (C$_6$F$_5$)$_4$B$^-$.

By an empty coordination site is meant a potential coordination site that does not have a ligand bound to it. Thus if an ethylene molecule is in the proximity of the empty coordination site, the ethylene molecule may coordinate to the metal atom.

By a ligand that may add to an olefin is meant a ligand coordinated to a metal atom into which an olefin molecule as described above (or a coordinated olefin molecule) may insert to start or continue a polymerization. For instance, this may take the form of the reaction (wherein L is a ligand and the olefin is ethylene):

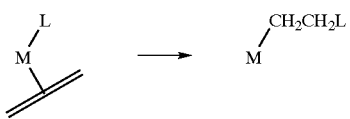

By a rare earth metal is meant one of lanthanum, cerium, praseodymium, neodymium, promethium, samarium, europium, gadolinium, terbium, dysprosium, holmium, erbium, thulium, ytterbium or lutetium.

Compounds of formulas (I) and (VII) can be made by the reaction of the corresponding bis(imidoyl chlorides) of oxalic acid with compounds containing primary or secondary amines, alcohols, phenols, thiols, phosphines, or a combination thereof, see for instance D. Lauder, et al., J. Prakt. Chem., vol. 337, p. 143–152 and ibid., p. 508–515 (1995), both of which are hereby included by reference, and the examples herein.

Compounds of formulas (II) and (III) may be made by the reaction of an organic isocyanate with the corresponding organic hydroxy compound, or primary or secondary amine, respectively.

The Ni and Pd and other metal complexes described herein may be made by various methods (depending on the other ligands present in the complex), and by methods described in World Patent Application 96/23010 and U.S. Pat. No. 5,714,556, both of which are hereby included by reference. The Examples herein also illustrate such methods. These complexes may be preformed, i.e., may be added to the polymerization process in a form in which the ligand (I), (II) or (III) is already complexed to the transition metal, or may be formed in situ, i.e., the transition metal (compound) and ligand are added separately to the polymerization process, but the desired complex forms in situ. This includes all instances when precursors to the desired transition metal complex are added. For instance the transition metal may be added in the form of an M[0] complex, such as bis(cyclooctadiene)nickel, in which the nickel may be oxidized to Ni[II] by reaction with HY, wherein Y is a relatively noncoordinating anion. Other methods of forming such complexes in situ are found in World Patent Application 96/23010 and U.S. Pat. No. 5,714,556.

In (I) and (VII), and in all other compounds in which these substituents occurs, it is preferred that:

A and E are each independently nitrogen or oxygen, more preferably both A and E are nitrogen; and/or A and E are both oxygen; and/or A is nitrogen or phosphorous, more preferably nitrogen, and R$^4$ and R$^5$ taken together for a ring; and/or R$^4$ and R$^6$ taken together form a ring, more preferably —(CH$_2$)$_z$— wherein z is 2 or 3; and/or R$^3$ is

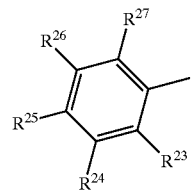

(VIII)

wherein R$^{23}$, R$^{24}$, R$^{25}$, R$^{26}$ and R$^{27}$ are each independently hydrogen, hydrocarbyl, substituted hydrocarbyl or a functional group, provided that any of R$^{23}$, R$^{24}$, R$^{25}$, R$^{26}$ and R$^{27}$ vicinal to one another taken together may form a ring; and/or $R^8$ is

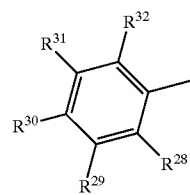

(IX)

wherein $R^{28}$, $R^{29}$, $R^{30}$, $R^{31}$ and $R^{32}$ are each independently hydrogen, hydrocarbyl, substituted hydrocarbyl or a functional group, provided that any of $R^{28}$, $R^{29}$, $R^{30}$, $R^{31}$ and $R^{32}$ vicinal to one another taken together may form a ring. In another preferred compound (I) or (VII) A and E taken together are part of a ring, where applicable in combination with any of the above.

In (II) or other compounds herein in which these groups occur, it is preferred that:

$Ar^1$ is

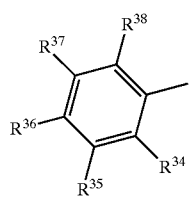

(X)

wherein $R^{34}$, $R^{35}$, $R^{36}$, $R^{37}$ and $R^{38}$ are each independently hydrogen, hydrocarbyl, substituted hydrocarbyl or a functional group, provided that any of $R^{34}$, $R^{35}$, $R^{36}$, $R^{37}$ and $R^{38}$ vicinal to one another taken together may form a ring, and more preferably one or both of $R^{34}$ and $R^{38}$ are alkyl containing 1 to 4 carbon atoms, and/or $R^{35}$, $R^{36}$ and $R^{37}$ are hydrogen; and/or $R^9$ is alkyl, substituted alkyl, aryl or substituted aryl, especially alkyl or

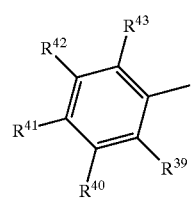

(XI)

wherein $R^{39}$, $R^{40}$, $R^{41}$, $R^{42}$ and $R^{43}$ are each independently hydrogen, hydrocarbyl, substituted hydrocarbyl or a functional group, provided that any of $R^{39}$, $R^{40}$, $R^{41}$, $R^{42}$ and $R^{43}$ vicinal to one another taken together may form a ring, and more preferably one or both of $R^{39}$ and $R^{43}$ are alkyl containing 1 to 4 carbon atoms, and/or $R^{40}$, $R^{41}$ and $R^{42}$ are hydrogen.

In (III) or other compounds herein in which these groups occur, it is preferred that:

$Ar^2$ is

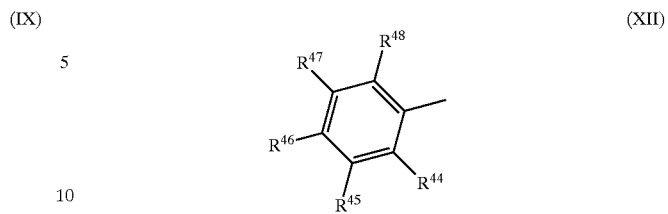

(XII)

wherein $R^{44}$, $R^{45}$, $R^{46}$, $R^{47}$ and $R^{48}$ are each independently hydrogen, hydrocarbyl, substituted hydrocarbyl or a functional group, provided that any of $R^{44}$, $R^{45}$, $R^{46}$, $R^{47}$ and $R^{48}$ vicinal to one another taken together may form a ring, and more preferably one or both of $R^{44}$ and $R^{48}$ are alkyl containing 1 to 4 carbon atoms, and/or $R^{45}$, $R^{46}$ and $R^{47}$ are hydrogen; and/or $R^{10}$ is alkyl or substituted alkyl, especially hydroxyl substituted alkyl.

It is preferred that X is halide, alkyl, carboxylate or acetylacetonate, more preferably chloride, bromide or iodide. When X is alkyl it is more preferred that M is Pd and only one of X is alkyl.

It is preferred that $R^1$ is hydrogen or n-alkyl containing 1 to 18 carbon atoms, more preferably hydrogen or methyl, and especially preferably hydrogen, or any combination thereof. It is also preferred that $R^2$ is $—(CH_2)_q R^{48}$ wherein q is 0 or an integer of 1 to 18 and $R^{48}$ is a functional group, more preferably q is 0 and/or $R^{48}$ is $CO_2 R^{49}$, wherein $R^{49}$ is hydrocarbyl or substituted hydrocarbyl, more preferably hydrocarbyl, and especially preferably alkyl.

In all complexes one preferred metal is nickel. In other complexes preferred metals are Ti, Zr, Sc, V, Cr or a rare earth metal, especially with (I) when $R^4$ and $R^5$ taken together form a ring, and $R^6$ and $R^7$ taken together do not form a ring.

In the first polymerization process described herein a nickel, palladium or other metal complex is either added to the polymerization process or formed in situ in the process. In fact, more than one such complex may be formed during the course of the process, for instance formation of an initial complex and then reaction of that complex to form a living ended polymer containing such a complex.

Examples of such complexes which may be formed initially in situ include

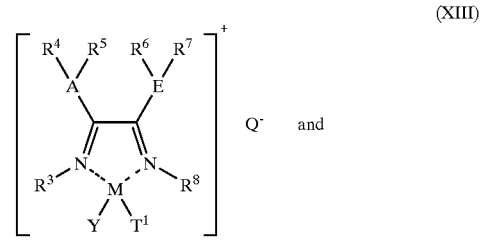

(XIII)

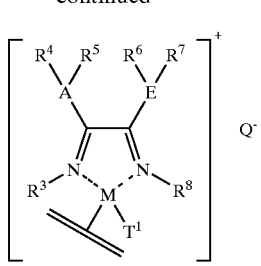

(XIV)

wherein R³ through R⁸ and M are as defined above, T¹ is hydride or alkyl or any other anionic ligand into which ethylene can insert, Y is a neutral ligand capable of being displaced by ethylene or a vacant coordination site, the "parallel lines" are an ethylene molecule coordinated to the metal, and Q is a relatively non-coordinating anion. Complexes may be added directly to the process or formed in situ. For instance, (XIII) may be formed by the reaction of (IV) with a neutral Lewis acid such as an alkyl aluminum compound. Another method of forming a complex in situ is adding a suitable nickel or palladium compound such as nickel [II] acetylacetonate, (I) and an alkyl aluminum compound. Other metal salts in which anions similar to acetylacetonate are present, and which may be removed by reaction with the Lewis or Bronsted acid, may also be used. For instance metal halides and carboxylates (such as acetates) may be used, particularly if they are slightly soluble in the process medium. It is preferred that these precursor metal salts be at least somewhat soluble in the process medium.

After the polymerization has started, the complex may be in a form such as

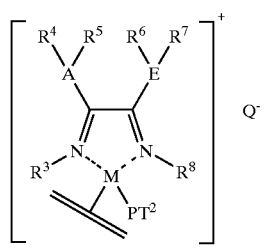

(XV)

wherein R³ through R⁸, M, and Q are as defined above, P is a divalent polymeric group such as a (poly)ethylene group of the formula —(CH$_2$CH$_2$)$_x$— wherein x is an integer of 1 or more, and T² is an end group, for example the groups listed for T¹ above. Those skilled in the art will note that (XV) is in essence a polymer containing a so-called living end. It is preferred that M be in +2 oxidation state in these compounds. Compounds such as (XIII), (XIV) and (XV) may or may not be stable away from an environment similar to that of the polymerization process, but they may be detected by NMR spectroscopy, particularly one or both of ¹H and ¹³C NMR, and particularly at lower temperatures. Such techniques, especially for polymerization "intermediates" of these types are known, see for instance World Patent Application 96/23010, especially Examples 197–203.

(XIII), (XIV) and (XV) may also be used, in the absence of any "co-catalysts" or "activators" to polymerize one or more suitable olefins in a third polymerization process. Except for the ingredients in the process, the process conditions for the third process, such as temperature pressure, polymerization medium, etc., may be the same as for the first and second polymerization processes, and preferred conditions for those processes are also preferred for the third polymerization process.

In the first, second and third polymerization processes herein, the temperature at which the polymerization is carried out is about −100° C. to about +200° C., preferably about −60° C. to about 150° C., more preferably about −20° C. to about 100° C. The pressure of the olefin (if it is a gas) at which the polymerization is carried out is not critical, atmospheric pressure to about 275 MPa being a suitable range.

The polymerization processes herein may be run in the presence of various liquids, particularly aprotic organic liquids. The catalyst system, olefin, and polyolefin may be soluble or insoluble in these liquids, but obviously these liquids should not prevent the polymerization from occurring. Suitable liquids include alkanes, cycloalkanes, selected halogenated hydrocarbons, and aromatic hydrocarbons. Specific useful solvents include hexane, toluene, benzene, methylene chloride, and 1,2,4-trichlorobenzene.

The olefin polymerizations herein may also initially be carried out in the solid state by, for instance, supporting the nickel or palladium compound on a substrate such as silica or alumina, activating it with the Lewis (such as W, for instance an alkylaluminum compound) or Bronsted acid and exposing it to olefin. Alternatively, the support may first be contacted (reacted) with W such as an alkylaluminum compound, and then contacted with an appropriate transition metal compound such as (IV), (V) or (VI). The support may also be able to take the place of the Lewis or Bronsted acid, for instance an acidic clay such as montmorillonite. Another method of making a supported catalyst is to start a polymerization or at least make a transition metal complex of another olefin or oligomer of an olefin such as cyclopentene on a support such as silica or alumina. These "heterogeneous" catalysts may be used to catalyze polymerization in the gas phase or the liquid phase. By gas phase is meant that a gaseous olefin is transported to contact with the catalyst particle.

In all of the polymerization processes described herein oligomers and polymers of the various olefins are made. They may range in molecular weight from oligomeric olefins, to lower molecular weight oils and waxes, to higher molecular weight polyolefins. One preferred product is a polymer with a degree of polymerization (DP) of about 10 or more, preferably about 40 or more. By "DP" is meant the average number of repeat (monomer) units in a polymer molecule.

Depending on their properties, the polymer made by the processes described herein are useful in many ways. For instance if they are thermoplastics, they may be used as molding resins, for extrusion, films, etc. if they are elastomeric, they may be used as elastomers. If they contain functionalized monomers such as acrylate esters, they are useful for other purposes, see for instance World Patent Application 96/23010.

Polyolefins are most often prepared by polymerization processes in which a transition metal containing catalyst system is used. Depending on the process conditions used and the catalyst system chosen, polymers, even those made from the same monomer(s) may have varying properties. Some of the properties which may change are molecular weight and molecular weight distribution, crystallinity, melting point, and glass transition temperature. Except for molecular weight and molecular weight distribution, branching can affect all the other properties mentioned.

It is known that certain transition metal containing polymerization catalysts including those disclosed herein, are especially useful in varying the branching in polyolefins made with them, see for instance World Patent Applications 96/23010 and 97/02298, and U.S. patent application Ser. No. 09/006,628, filed Jan. 13, 1998, and Ser. No. 09/006,536, filed Jan. 13, 1998. It is also known that blends of distinct polymers, that vary for instance in the properties listed above, may have advantageous properties compared to "single" polymers. For instance it is known that polymers with broad or bimodal molecular weight distributions may be melt processed (be shaped) more easily than narrower molecular weight distribution polymers. Similarly, thermoplastics such as crystalline polymers may often be toughened by blending with elastomeric polymers.

Therefore, methods of producing polymers which inherently produce polymer blends are useful especially if a later separate (and expensive) polymer mixing step can be avoided. However in such polymerizations one should be aware that two different catalysts may interfere with one another, or interact in such a way as to give a single polymer.

In such a process the catalysts disclosed herein can be termed the first active polymerization catalyst. Monomers useful with these catalysts are those described (and also preferred) above.

A second active polymerization catalyst (and optionally one or more others) is used in conjunction with the first active polymerization catalyst. The second active polymerization catalyst may be another late transition metal catalyst, for example as described in World Patent Applications 96/23010 and 97/02298, and U.S. patent application Ser. No. 09/006,628, filed Jan. 13, 1998, Ser. No. 09/006,536, filed Jan. 13, 1998, and Ser. No. 08/991,372, filed Dec. 16, 1997. Other useful types of catalysts may also be used for the second active polymerization catalyst. For instance so-called Ziegler-Natta and/or metallocene-type catalysts may also be used. These types of catalysts are well known in the polyolefin field, see for instance Angew. Chem., Int. Ed. Engl., vol. 34, p. 1143–1170 (1995), European Patent Application 416,815 and U.S. Pat. No. 5,198,401 for information about metallocene-type catalysts, and J. Boor Jr., Ziegler-Natta Catalysts and Polymerizations, Academic Press, New York, 1979 for information about Ziegler-Natta-type catalysts, all of which are hereby included by reference. Many of the useful polymerization conditions for all of these types of catalysts and the first active polymerization catalysts coincide, so conditions for the polymerizations with first and second active polymerization catalysts are easily accessible. Oftentimes the "co-catalyst" or "activator" is needed for metallocene or Ziegler-Natta-type polymerizations. In many instances the same compound, such as an alkylaluminum compound, may be used as an "activator" for some or all of these various polymerization catalysts.

In one preferred process described herein the first olefin(s) [the monomer(s) polymerized by the first active polymerization catalyst] and second olefin(s) [the monomer(s) polymerized by the second active polymerization catalyst] are identical, and preferred olefins in such a process are the same as described immediately above. The first and/or second olefins may also be a single olefin or a mixture of olefins to make a copolymer. Again it is preferred that they be identical particularly in a process in which polymerization by the first and second active polymerization catalysts make polymer simultaneously.

In some processes herein the first active polymerization catalyst may polymerize a monomer that may not be polymerized by said second active polymerization catalyst, and/or vice versa. In that instance two chemically distinct polymers may be produced. In another scenario two monomers would be present, with one polymerization catalyst producing a copolymer, and the other polymerization catalyst producing a homopolymer, or two copolymers may be produced which vary in the molar proportion or repeat units from the various monomers. Other analogous combinations will be evident to the artisan.

In another variation of this process one of the polymerization catalysts makes an oligomer of an olefin, preferably ethylene, which oligomer has the formula $R^{70}CH=CH_2$, wherein $R^{70}$ is n-alkyl, preferably with an even number of carbon atoms. The other polymerization catalyst in the process them (co)polymerizes this olefin, either by itself or preferably with at least one other olefin, preferably ethylene, to form a branched polyolefin. Preparation of the oligomer (which is sometimes called an $\alpha$-olefin) by a second active polymerization-type of catalyst can be found in World Patent Application 96/23010, and U.S. patent application Ser. No. 09/005,965, filed Jan. 12, 1998.

Likewise, conditions for such polymerizations, using catalysts of the second active polymerization type, will also be found in the appropriate above mentioned references.

Two chemically different active polymerization catalysts are used in this polymerization process. The first active polymerization catalyst is described in detail above. The second active polymerization catalyst may also meet the limitations of the first active polymerization catalyst, but must be chemically distinct. For instance, it may have a different transition metal present, and/or utilize a different type of ligand and/or the same type of ligand which differs in structure between the first and second active polymerization catalysts. In one preferred process, the ligand type and the metal are the same, but the ligands differ in their substituents.

Included within the definition of two active polymerization catalysts are systems in which a single polymerization catalyst is added together with another ligand, preferably the same type of ligand, which can displace the original ligand coordinated to the metal of the original active polymerization catalyst, to produce in situ two different polymerization catalysts.

The molar ratio of the first active polymerization catalyst to the second active polymerization catalyst used will depend on the ratio of polymer from each catalyst desired, and the relative rate of polymerization of each catalyst under the process conditions. For instance, if one wanted to prepare a "toughened" thermoplastic polyethylene that contained 80% crystalline polyethylene and 20% rubbery polyethylene, and the rates of polymerization of the two catalysts were equal, then one would use a 4:1 molar ratio of the catalyst that gave crystalline polyethylene to the catalyst that gave rubbery polyethylene. More than two active polymerization catalysts may also be used if the desired product is to contain more than two different types of polymer.

The polymers made by the first active polymerization catalyst and the second active polymerization catalyst may be made in sequence, i.e., a polymerization with one (either first or second) of the catalysts followed by a polymerization with the other catalyst, as by using two polymerization vessels in series. However it is preferred to carry out the polymerization using the first and second active polymerization catalysts in the same vessel(s), i.e., simultaneously. This is possible because in most instances the first and second active polymerization catalysts are compatible with each other, and they produce their distinctive polymers in the other catalyst's presence. Any of the processes applicable to the individual catalysts may be used in this polymerization process with 2 or more catalysts, i.e., gas phase, liquid phase, continuous, etc.

The polymers produced by this process may vary in molecular weight and/or molecular weight distribution and/or melting point and/or level of crystallinity, and/or glass transition temperature and/or other factors. For copolymers the polymers may differ in ratios of comonomers if the different polymerization catalysts polymerize the monomers present at different relative rates. The polymers produced are useful as molding and extrusion resins and in films as for packaging. They may have advantages such as improved melt processing, toughness and improved low temperature properties.

Hydrogen may be used to lower the molecular weight of polyolefin produced in the first or second processes. It is preferred that the amount of hydrogen present be about 0.01 to about 50 mole percent of the olefin present, preferably about 1 to about 20 mole percent. When liquid monomers (olefins) are present, one may need to experiment briefly to find the relative amounts of liquid monomers and hydrogen (as a gas). If both the hydrogen and monomer(s) are gaseous, their relative concentrations may be regulated by their partial pressures.

In the Examples, certain abbreviations are used:

ΔH$_f$—heat of fusion
BAF—tetrakis[bis(3,5-trifluoromethyl)phenyl]borate
DMAP—4-dimethylaminopyridine
DSC—Differential Scanning Calorimetry (at a heating rate of 15° C./min; first heat −150° C. to +160° C., second heat −150° C. to +250° C.)
EOC—end of chain
Et—ethyl
GPC—Gel Permeation Chromatography
MAO and PMAO—methylaluminoxane
Me—methyl
Mn—number average molecular weight
Mw—weight average molecular weight
PDI—polydispersity, Mw/Mn
RT—room temperature
TLC—Thin Layer Chromatography
Tg—glass transition temperature
Tm=melting point
TO—turnovers, moles of olefin polymerized per mole of transition metal compound All pressures in the Examples are gauge pressures. Metal complexes are designated by the number of the ligand, the metal, and other ligands (neutral or charged) on the complex. For instance the complex of ligand 4 with NiBr$_2$ is written as 4.NiBr$_2$.

In the Examples, certain compounds are made and/or used. Their structures are shown below.

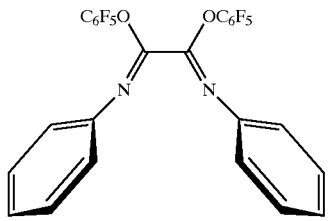

1

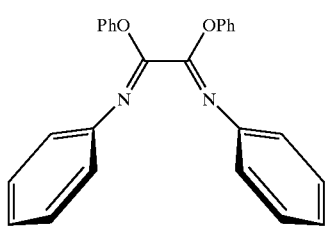

2

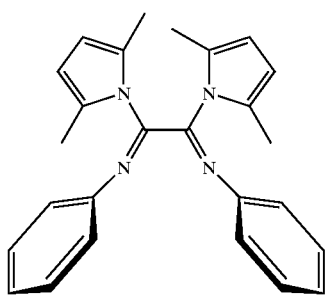

3

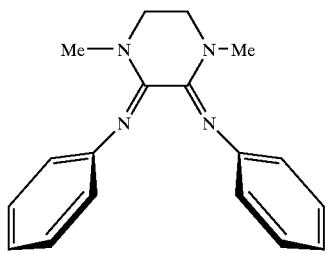

4

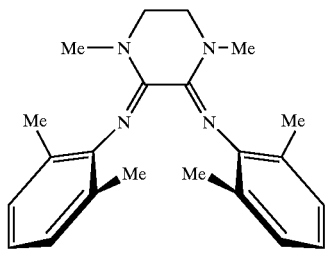

5

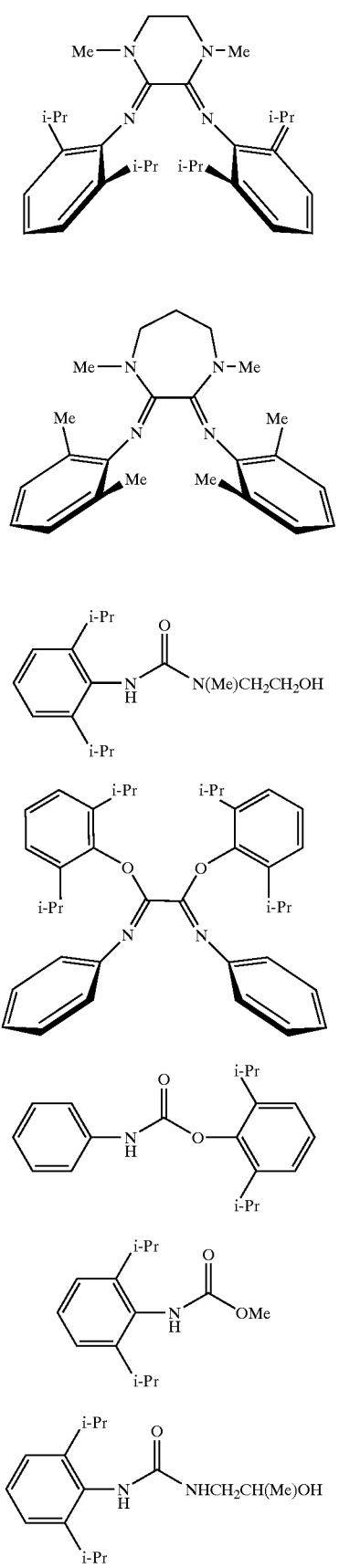

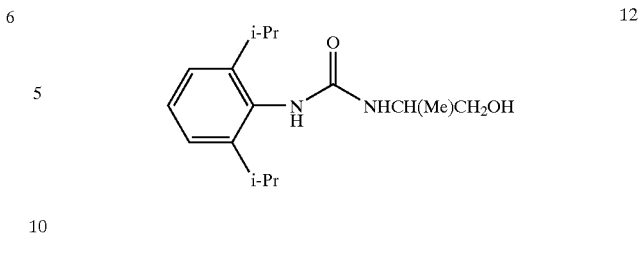

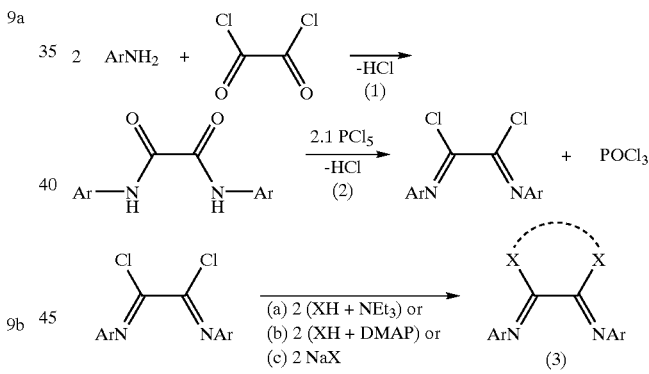

EXAMPLES 1–13

Compounds 1–13 were synthesized according to equations 1–3 shown below. These syntheses are based upon literature methods: see (a) Lindauer, D.; Beckert, R.; Doring, M.; Fehling, P.; Gorls, H. *J. Prakt. Chem.* 1995, 337, 143–152 and references therein and (b) Lindauer, D.; Beckert, R.; Billert, T.; Doring, M.; Gorls, H. *J. Prakt. Chem.* 1995, 337, 508–515 and references therein. Compounds 8, 9b, 10, 11, 12 and 13 are hydrolysis products of the ArN=C(X)—C(X)=NAr product shown in equation 3.

EXAMPLE 1

Synthesis of 1

In a drybox, a 50 mL round-bottom flask was charged with PhN=C(Cl)—C(Cl)=NPh (0.693 g, 2.5 mmol), pentafluorophenol (0.965 g, 5 mmol), DMAP (0.615 g, 5 mmol) and anhydrous toluene (15 mL) and stoppered. The flask was moved to the hood and refluxed under $N_2$ for about 3 h, while the reaction was monitored by TLC (5% ethyl acetate/hexane). The precipitate (DMAP.HCl) was removed by filtration and rinsed well with toluene. Solvent removal yield an oily solid, which was purified by column chromatography (silica gel, 5% ethyl acetate/hexane). A white solid (0.822 g, 57%) was obtained: $^1$H NMR (CDCl$_3$) δ 7.15 (m, 6, H$_{Ph}$), 6.52 (m, 4, H$_{Ph}$); $^{13}$C NMR (CDCl$_3$) δ 146.5 and 143.25 (N=C—C=N and Ph: C$_{ipso}$), 142.1 (d of d, J=248, C$_6$F$_5$: C$_o$), 140.5 (d of t, J=258, C$_6$F$_5$: C$_p$), 138.8 (d of t, J=253, $C_6F_5$: $C_m$), 128.8, 125.7 and 120.6 (Ph: $C_o$, $C_m$, and $C_p$); $^{19}F$ NMR (CDCl$_3$) δ −151.6 (d, $F_o$), −158.02 (t, $F_p$), −162.6 (t, $F_m$). [No peak was apparent in the $^1H$ NMR spectrum that would be indicative of the NH proton of the potential hydrolysis product PhNHC(O) (OC$_6$F$_5$).]

EXAMPLE 2

Synthesis of 2

In a hood, a 100 mL round-bottom flask was charged with PhN=C(Cl)—C(Cl)=NPh (1.111 g, 4 mmol), tetrabutylammonium chloride (0.078 g, 0.2 mmol), phenol (0.760 g, 8 mmol) and methylene chloride (20 mL). Sodium hydroxide (400 µL, 25 M) and water (500 µL) were added via syringe. The reaction was refluxed gently until starting material had disappeared by TLC (5% ethyl acetate/hexane). The aqueous layer was extracted with methylene chloride (3×10 mL) and the organic layers were combined and dried over MgSO$_4$. The solvent was removed in vacuo and the product was recrystallized from hot hexane. After drying the product under vacuum, 1.006 g (64%) of white powder was obtained: $^1H$ NMR (CDCl$_3$) δ 7.29 (t, 2, $H_m$), 7.17 (t, 2, $H'_m$), 7.12 (t, 1, $H_p$), 7.03 (t, 1, $H'_p$), 6.95 (d, 2, $H_o$), 6.69 (d, 2, $H'_o$); $^{13}C$ NMR (CDCl$_3$) δ 151.9, 151.3, and 145.0 ($C_{ipso}$, $C'_{ipso}$, N=C—C=N), 129.4, 128.5, 125.8, 124.5, 121.8, and 121.1 (Ph: $C_o$, $C_m$, $C_p$; Ph': $C_o$, $C_m$, $C_p$). [No peak was apparent in the $^1H$ NMR spectrum that would be indicative of the NH proton of the potential hydrolysis product PhNHC(O)(OPh).]

EXAMPLE 3

Synthesis of 3

In a drybox, a small vial was charged with 0.277 g (1 mmol) of PhN=C(Cl)—C(Cl)=NPh, the sodium salt of 2,5-dimethylpyrrole (0.239 g, 2 mmol) and anhydrous tetrahydrofuran (10 mL) and capped. The vial was transferred to the hood and the reaction was allowed to stir at RT and monitored by TLC (5% ethyl acetate/hexane) until no starting material was present (about 24 h). The reaction was filtered to remove the NaCl precipitate, which was then rinsed with THF. The solvent was removed under vacuum and the product was purified by column chromatography (silica gel, 5% ethyl acetate/hexane). A solid (0.145 g, 37%) was obtained: $^1H$ NMR (THF-d$_8$) δ 7.3–7.0 (m, 6, Ph: $H_m$ and $H_p$), 6.62 (d, 4, Ph: $H_o$), 5.75 (s, 4, $H_{pyrrole}$), 2.05 (s, 12, Me); $^{13}$C/APT NMR (CDCl$_3$) δ 147.9 and 145.3 (Ph: $C_{ipso}$ and N=C—C=N), 127.2 (pyrrole: C—Me), 128.4, 127.6, and 123.6 (Ph: $C_o$, $C_m$, and $C_p$); 107.6 (pyrrole: CH), 13.1 (Me). [No peak was apparent in the $^1H$ NMR spectrum that would be indicative of the NH proton of the potential hydrolysis product PhNHC(O)(2,5-dimethylpyrrole).

EXAMPLE 4

Synthesis of 4

In a drybox, a small vial was charged with 2.080 g (7.5 mmol) of PhN=C(Cl)—C(Cl)=NPh and anhydrous toluene (10 mL). Triethylamine (2.10 µL, 15 mmol) was added via syringe and capped. The vial was transferred to the hood and N,N'-dimethylethylenediamine (800 µL, 7.5 mmol) was added via syringe. The reaction became very warm and a precipitate formed quickly. The reaction mixture was allowed to stir for about 24 h and then filtered to remove NEt$_3$.HCl, which was rinsed well with toluene. The solvent was removed under vacuum to give an oil. Diethyl ether was added to precipitate a solid, which was collected on a frit. A pale yellow orange powder (1.336 g, 47%) was isolated: $^1H$ NMR (CDCl$_3$) δ 6.85 (t, 4, $H_m$), 6.74 (t, 2, $H_p$), 6.10 (t, 4, $H_o$), 3.82 and 3.02 (br s of 2H and overlapping br and sharp singlets of 8H, CH$_2$ and Me); $^{13}C$ NMR (CDCl$_3$) δ 148.6 and 148.2 (Ph: $C_{ipso}$ and N=C—C=N), 128.0, 121.7 and 121.3 (Ph: $C_o$, $C_m$, and $C_p$), 49.8 (CH$_2$), 36.4 (NCH$_3$); MW calcd for $C_{18}H_{20}N_4$ 292.39 g/mol; MS (CIMS) 293.0 m/z (M+1).

EXAMPLE 5

Synthesis of 5

In a drybox, a 50 mL round-bottom flask was charged with 1.666 g (5 mmol) of ArN=C(Cl)—C(Cl)=NAr (Ar= 2,6-C$_6$H$_3$—Me$_2$) and anhydrous toluene (10 mL). Triethylamine (1.4 mL, 10 mmol) was added via syringe and capped. The flask was transferred to the hood where N,N'-dimethylethylenediamine (540 µL 5 mmol) was added via syringe. The reaction was allowed to stir at RT for about 48 h; at this point, TLC (5% ethyl acetate/hexane) indicated that starting material was still present. Therefore, the reaction was heated gently for about 24 h and checked again by TLC. The precipitate (NEt$_3$.HCl) was removed via filtration and rinsed well with toluene. The solvent was removed under vacuum. Diethyl ether was added to precipitate the product, which was collected. The filtrate was reduced in volume and hexane added to precipitate more of the product. All fractions were combined and rinsed with hexane, collected and dried under vacuum. The product (0.782 g, 45%) was isolated as a pale yellow powder. $^1H$ and $^{13}C$ NMR resonances are broad at RT and are therefore reported at 60° C., where they are sharper: $^1H$ NMR (CDCl$_3$, 60° C.) δ 6.84 (d, 4, $H_m$), 6.68 (t, 2, $H_p$), 3.41 (s, 4, CH$_2$), 2.78 (s, 6, NMe), 1.86 (s, 12, Ar: Me); $^{13}$C/APT NMR (CDCl$_3$, 60° C.) δ 148.4 and 145.5 (Ar: $C_{ipso}$ and N=C—C=N), 127.2 (Ar: $C_m$), 126.9 (Ar: $C_o$), 120.7 (Ar: $C_p$), 49.3 (CH$_2$), 37.2 (NMe), 18.2 (Ar: Me); MW calcd for $C_{22}H_{28}N_4$ 348.5 g/mol; MS (CIMS) 349.1 m/z (M+1).

EXAMPLE 6

Synthesis of 6

In a drybox, a small vial was charged with 2.232 g (5 mmol) of ArN=C(Cl)—C(Cl)=NAr (Ar=2,6-C$_6$H$_3$-(i-Pr)$_2$), DMAP (1.222 g, 10 mmol) and anhydrous toluene (10 mL) and capped. The vial was transferred to the hood and N,N'-dimethylethylenediamine (532 µL, 5 mmol) was added via syringe. The reaction mixture became clear and then after approximately 5 min a precipitate formed. The reaction mixture was allowed to stir at RT for approximately 2 days and followed by TLC (5% ethyl acetate/hexane). CH$_2$Cl$_2$ was added to the reaction mixture to dissolve the precipitate and the resulting solution was extracted with 5% HCl (aq) (3×25 mL), and the organic layer was dried over MgSO$_4$.

The solvent was removed under vacuum and the resulting solid was recrystallized from hot hexane to give 0.843 g (37%) of a pale yellow powder: $^1$H NMR (CDCl$_3$) δ 7.5–7.0 (m, 6, H$_{aryl}$), 3.56 (s, 4, CH$_2$), 3.14 (s, 6, NMe), 3.08 (septet, 4, CHMe$_2$), 1.17 (d, 24, CHMe$_2$)

EXAMPLE 7

Synthesis of 7

In a drybox, a 50 mL round-bottom flask was charged with 1.666 g (5 mmol) of ArN=C(Cl)—C(Cl)=NAr (Ar= 2,6-C$_6$H$_3$—Me$_2$) and anhydrous toluene (10 mL). Triethylamine (1.4 mL, 10 mmol) was added via syringe and the flask was capped and transferred to the hood. In the hood, N,N'-dimethyl-1,3-propanediamine (630 μL, 5 mmol) was added via syringe. The reaction mixture was allowed to stir at RT for about 48 h; at this point, TLC (5% ethyl acetate/hexane) showed that starting material was still present. Therefore, the reaction was heated gently for about 24 h and checked again by TLC. The precipitate (NEt$_3$.HCl) was removed via filtration and rinsed well with toluene. The solvent was removed under vacuum. Diethyl ether was added to precipitate the product, which was collected. The filtrate was reduced in volume and hexane added to further precipitate the product. All fractions were combined and rinsed with hexane, collected and dried under vacuum to give 0.844 g (47%) of an off-white powder: $^1$H NMR (CDCl$_3$, 500 MHz, RT) δ 6.71 (br s, 4, H$_m$), 6.61 (t, 2, H$_p$), 1.79 (pentet, 2, CH$_2$CH$_2$CH$_2$); the following resonances correspond to the NMe, Ar: Me, and —CH$_2$CH$_2$CH$_2$— resonances: 3.63 (br s), 3.07 (br s), 2.75 (br s), 2.01 (br s), 1.30 (br s); $^{13}$C NMR/APT (CD$_2$Cl$_2$) δ 151, 146.7, and 130.4 (Ar: C$_{ipso}$, C$_o$, and N=C—C=N), 127.1 (Ar: C$_m$), 121.3 (Ar: C$_p$), 47.9 (NCH$_2$CH$_2$CH$_2$N), 36.0 (NMe), 24.5 (NCH$_2$CH$_2$CH$_2$N), 17.6 (Ar: Me); MW calcd for C$_{23}$H$_{30}$N$_4$ 362.5 g/mol; MS (CIMS) 363.0 m/z (M+1).

EXAMPLE 8

Synthesis of 8

In a drybox, a small vial was charged with 2.232 g (5 mmol) of ArN=C(Cl)—C(Cl)=NAr (Ar=2,6-C$_6$H$_3$—(i-Pr)$_2$), DMAP (1.229 g, 10 mmol) and anhydrous toluene (10 mL) and capped. In the hood, 2-(methylamino)ethanol (420 μL, 5 mmol) was added via syringe. The reaction mixture was allowed to stir at RT for about 48 h and monitored by TLC (5% ethyl acetate/hexane). Next, the reaction mixture was diluted in CH$_2$Cl$_2$ and the resulting solution was extracted with 5% HCl(aq) (3×25 mL), and the organic layer was dried over MgSO$_4$. After solvent removal, the product was washed with hexane and then dried in vacuo to give 0.986 g of a pale yellow solid: $^1$H NMR (CDCl$_3$) δ 7.40–6.56 (m, 3, H$_{aryl}$), 6.31 (s, 1, NH or OH), 3.65 (t, 2, CH$_2$), 3.41 (t, 2, CH$_2$), 2.99 (septet, 2, CHMe$_2$), 2.92 (s, 3, Me), 1.08 (m, 12, CHMe$_2$). [The product contains some impurities that make some NMR assignments, particularly integrations, uncertain. The structure of the compound is proposed to be the hydrolysis product shown above on the basis of the appearance of the 6.31 ppm —NH or —OH resonance.]

EXAMPLE 9

Synthesis of 9a and 9b

In a drybox, a small vial was charged with 0.831 g (3 mmol) of PhN=C(Cl)—C(Cl)=NPh, sodium 2,6-diisopropylphenoxide (1.201 g, 6 mmol) and anhydrous tetrahydrofuran (10 mL) and capped. The vial was transferred to the hood, and the reaction mixture was allowed to stir at RT for approximately 2 days, until TLC (5% ethyl acetate/hexane) showed no starting material. Sodium chloride was removed by filtration and rinsed well with THF. The solvent was removed under vacuum and the remaining solid was recrystallized from hot hexane. The product was isolated and dried in vacuo to yield 1.326 g (79%) of a yellow-orange solid as a mixture of 9a and 9b in a 6.7 to 1 ratio. 9a: $^1$H NMR (CDCl$_3$) δ 7.2–6.5 (m, 16, H$_{aryl}$), 2.99 (septet, 4, CHMe$_2$), 1.13 (d, 12, CHMeMe'), 1.06 (d, 12, CHMeMe'); $^{13}$C/APT NMR (CDCl$_3$) δ 151.0, 146.7, 145.2, and 140.9 (Ph: C$_{ipso}$; Ar: C$_{ipso}$, C$_o$; N=C—C=N), 128.2, 125.6, 124.1 and 120.6 (Ph: C$_o$, C$_m$, C$_p$; Ar: C$_m$, C$_p$), 26.9 (CHMe$_2$), 24.1 and 23.3 (CHMeMe'); MW calcd for C$_{38}$H$_{44}$N$_2$O$_2$ 560.79 g/mol; MS (CIMS) 561.4 m/z (M+1). 9b: $^1$H NMR (CDCl$_3$, non-aromatic resonances only) δ 4.69 (NH), 3.08 (septet, 2, CHMe$_2$), 1.20 (d, 12, CHMe$_2$); MW calcd for Cl$_{19}$H$_{23}$O$_2$N 297.4 g/mol; MS (CIMS) 297.9 m/z (M+1).

EXAMPLE 10

Synthesis of 10

In a drybox, a small vial was charged with 3.341 g (7.5 mmol) of ArN=C(Cl)—C(Cl)=NAr (Ar=2,6-C$_6$H$_3$—(i-Pr)$_2$), anhydrous sodium methoxide (0.854 g, 15.75 mmol), and anhydrous methanol (10 mL) and capped. The vial was transferred to the hood, and the reaction mixture was allowed to stir at RT for about 3 days until TLC showed little starting material present. The white solid was filtered off and rinsed with methanol. Next, the solvent was removed and the product was dried under vacuum. The solid was then washed with hexane and dried in vacuo. A white crystalline solid (1.446 g, 44%) was obtained. Restricted rotation about the amide bond results in the observation of two rotamers at RT in approximately a 1.16 to 1 ratio. Only one set of resonances is observed at 60° C.: $^1$H NMR (CDCl$_3$, RT, 500 MHz) δ 7.33 (t, 1, Ar: H$_p$), 7.21 (d, 2, Ar: H$_m$), 6.49 and 6.10 (s, NH and NH'), 3.82 and 3.69 (OMe and OMe'), 3.22 (br s, 2, CHMe$_2$), 1.25 (d, 12, CHMe$_2$); $^1$H NMR (CDCl$_3$, 60° C., 500 MHz) δ 7.32 (t, 1, Ar: H$_p$), 7.20 (d, 2, Ar: H$_m$), 6.08 (br s, 1, NH), 3.76 (br s, 3, OMe), 3.23 (septet, 2, CHMe$_2$), 1.26 (d, 12, CHMe$_2$); $^{13}$C NMR (CDCl$_3$, RT, 125 MHz) δ 156.3, 146.9 and 131.1 (Ar: C$_{ipso}$, C$_o$; C=O), 127.9 and 123.5 (Ar: C$_m$, C$_p$), 52.4 (OCH$_3$), 28.6 (CHMe$_2$), 23.5 (CHMe$_2$); MW calcd for C$_{14}$H$_{21}$O$_2$N 235.33 g/mol; MS (CIMS) 236.0 m/z (M+1).

EXAMPLE 11

Synthesis of 11

In the drybox, a small vial was charged with 2.229 g (5 mmol) of ArN=C(Cl)—C(Cl)=NAr (Ar=2,6-C$_6$H$_3$—(i-Pr)$_2$), triethylamine (1.4 mL, 10 mmol), 1-aminopropanol (400 μL, 5 mmol), and anhydrous toluene (10 mL) and capped. The reaction mixture was allowed to stir at RT for about 7 days. During this time, a precipitate (NEt$_3$.HCl) formed, which was removed via filtration and rinsed well with toluene. The solvent was removed under vacuum, and the product was washed with hexane and pumped dry to give 0.444 g (20%) of a pale yellow powder: $^1$H NMR (CDCl$_3$) δ 7.26 (t, 1, H$_p$), 7.14 (d, 2, H$_m$), 6.15 and 4.52 (s, 1 each, NH, NH' or OH), 3.75 (m, 1, CHMeO), 3.23 (m, 3, CHH'NH and CHMe$_2$), 3.00 (m, 2, CHH'NH), 1.14 (m, 12, CHMe$_2$), 1.03 (d, 3, CHMeO); $^{13}$C/APT NMR (CDCl$_3$) 159.1, 147.9 and 130.8 (C=O, Ar: C$_{ipso}$, C$_o$), 129.0 (Ar: C$_p$), 124.1 (Ar: C$_m$), 68.2 (OCHMe), 47.9 (CH$_2$) 28.3 (CHMe$_2$), 24.3 and 23.1 (CHMeMe'), 20.6 (OCHMe); MW calcd for C$_{16}$H$_{26}$O$_2$N$_2$ 278.40 g/mol; MS (CIMS) 279.0 m/z (M+1).

EXAMPLE 12

Synthesis of 12

In a drybox, a small vial was charged with 2.234 g (5 mmol) of ArN=C(Cl)—C(Cl)=NAr (Ar=2,6-C$_6$H$_3$—(i-Pr)$_2$), triethylamine (1.4 mL, 10 mmol), dl-alaninol (400 μL, 5 mmol), and anhydrous toluene (10 mL) and capped. The reaction mixture was allowed to stir at RT for about 48 h during which time a thick precipitate formed. Next, the precipitate (NEt$_3$.HCl) was removed via filtration and rinsed well with toluene. The solvent was removed under vacuum and the product was washed with hexane and dried in vacuo to give 0.592 g (26%) of a pale yellow powder: $^1$H NMR (CDCl$_3$) δ 7.27 (t, 1, H$_p$), 7.15 (d, 2, H$_m$), 6.03 and 4.18 (s, 1 each, NH, NH' or OH), 3.86 (m, 1, CHMeN), 3.50 (m, 1, CHH'O), 3.36 (m, 1, CHH'O), 3.20 (m, 2, CHMe$_2$), 1.12 (m, 12, CHMe$_2$), 0.98 (d, 3, CHMeNH); $^{13}$C/APT NMR (CDCl$_3$) δ 157.1, 147.7, 130.7 (C=O, Ar: C$_{ipso}$, C$_o$), 128.8 (Ar: C$_p$), 123.2 (Ar: C$_m$), 67.6 (CH$_2$), 48.3 (CHMeN), 28.1 (CHMe$_2$), 24.6 and 24.3 (CHMeMe'), 17.2 (CHMeN); MW calcd for C$_{16}$H$_{26}$O$_2$N$_2$ 278.40 g/mol; MS (CIMS) 279.0 m/z (M+1).

EXAMPLE 13

Synthesis of 13

In a drybox, a small vial was charged with 2.229 g (5 mmol) of ArN=C(Cl)—C(Cl)=NAr (Ar=2,6-C$_6$H$_3$—(i-Pr)$_2$), triethylamine (1.40 mL, 10 mmol), 3-amino-1-propanol (400 μL, 5 mmol), and anhydrous toluene (10 mL) and capped. The reaction mixture was allowed to stir at RT for about 3–4 days during which time a thick precipitate formed. The reaction mixture was diluted with CH$_2$Cl$_2$ and the resulting solution was extracted with 5% HCl (aq) (3×25 mL) and dried over MgSO$_4$. The solvent was removed and the product was washed with hexane and dried in vacuo to yield 0.592 g (26%) of a white powder: $^1$H NMR (CDCl$_3$) 7.37 (t, 1, H$_p$), 7.24 (d, 2, H$_m$), 6.40 4.45 and 4.04 (br s, 1 each, NH, NH' and OH), 3.64 (t, 2, CH$_2$), 3.37 (t, 2, CH$_2$), 3.30 (septet, 2, CHEMe$_2$), 1.59 (pentet, 2, CH$_2$), 1.22 (br m, 12, CHMe$_2$); $^{13}$C/APT NMR (CDCl$_3$) δ 158.8, 145.6 and 128.8 (C=O; Ar: C$_{ipso}$, C$_o$), 125.7 (Ar: C$_p$), 123.3 (Ar: C$_m$), 58.2, 33.7 and 32.9 (CH$_2$CH$_2$CH$_2$), 28.2 (CHMe$_2$), 24.1 and 22.8 (CHMeMe'); MW calcd for C$_{16}$H$_{26}$O$_2$N$_2$ 278.40 g/mol; MS (CIMS) 279.0 m/z (M+1).

EXAMPLE 14

Synthesis of 5.PdMeCl

In the drybox, compound 5 (255 mg, 0.731 mmol) and CODPdMeCl (194 mg, 0.731 mmol) were dissolved in ~15 mL of CH$_2$Cl$_2$. After being stirred overnight, the reaction mixture was filtered and the solvent was removed in vacuo. The resulting yellow powder was washed with Et$_2$O and dried (272 mg, 73.5%): $^1$H NMR (CD$_2$Cl$_2$) δ 7.4–7.0 (m, 6, H$_{aryl}$), 3.57 (s, 4, NCH$_2$CH$_2$N'), 2.68 and 2.67 (s, 3 each, NMe, N'Me), 2.62 and 2.59 (s, 6 each, Ar, Ar': Me), 0.00 (s, 3, PdMe).

EXAMPLE 15

Synthesis of 7.PdMeCl

In the drybox, compound 7 (113 mg, 0.312 mmol) and CODPdMeCl (82.6 mg, 0.312 mmol) were suspended in ~15 mL of Et$_2$O. After being stirred overnight, the reaction mixture was allowed to settle and the solvent was decanted. The resulting yellow powder was washed twice more with Et$_2$O and then dried in vacuo (92.6 mg, 57.1%): $^1$H NMR (CD$_2$Cl$_2$) δ 7.2–7.0 (m, 6, H$_{aryl}$), 3.35 (t, 4, NCH$_2$CH$_2$CH$_2$N), 2.51 and 2.46 (s, 6 each, Ar, Ar': Me), 2.40 and 2.38 (s, 3 each, NMe, N'Me), 2.08 (pentet, 2, NCH$_2$CH$_2$CH$_2$N'), 0.00 (s, 3, PdMe).

EXAMPLE 16

Synthesis of [5.Pd(Me)(NCMe)]BAF

In the drybox at RT, 1 mL of CH$_3$CN and 14 mL of Et$_2$O were added to a mixture of 5.PdMeCl (272 mg, 0.538 mmol) and NaBAF (476 mg, 0.538 mmol). The reaction mixture was stirred overnight, sodium chloride was removed via filtration, and the solvent was removed in vacuo to give 595 mg (80.5%) of a pale orange powder: $^1$H NMR (CD$_2$Cl$_2$) δ 7.83 (s, 8, BAF: H$_o$), 7.67 (s, 4, BAF: H$_p$), 7.3–6.9 (m, 6, H$_{aryl}$), 3.49 (s, 4, NCH$_2$CH$_2$N'), 2.65 and 2.56 (s, 3 each, NMe, N'Me), 2.45 and 2.37 (s, 6 each, Ar, Ar': Me), 1.76 (NCMe), 0.00 (PdMe).

EXAMPLE 17

Synthesis of [7.Pd(Me)(NCMe)]BAF

In the drybox at RT, 1 mL of CH$_3$CN and 14 mL of Et$_2$O were added to a mixture of 7.PdMeCl (92.6 mg, 0.178 mmol) and NaBAF (158 mg, 0.178 mmol). The reaction mixture was stirred overnight, sodium chloride was removed via filtration, and the solvent was removed in vacuo to give 201 mg (81.4%) of a yellow powder: $^1$H NMR (CD$_2$Cl$_2$) δ 7.69 (s, 8, BAF: H$_o$), 7.51 (s, 4, BAF: H$_p$), 7.2–6.9 (m, 6, H$_{aryl}$), 3.29 and 3.27 (t, 2 each, NCH$_2$CH$_2$CH$_2$N'), 2.37 and 2.29 (s, 3 each, NMe, N'Me), 2.35 and 2.28 (s, 6 each, Ar, Ar': Me), 1.98 (pentet, 2, NCH$_2$CH$_2$CH$_2$N'), 1.64 (s, 3, NCMe), 0.01 (s, 3, PdMe).

EXAMPLE 18

Ethylene Polymerization by [5.Pd(Me)(NCMe)]BAF

A 40 mL CH$_2$Cl$_2$ solution of [5.Pd(Me)(NCMe)]BAF (137 mg, 0.1 mmol) was stirred and placed under 0 kPa (1 atm) of ethylene for 72 h. Following precipitation of the reaction mixture into methanol, filtration, and vacuum drying, polyethylene (6.35 g; 2,264 TO) was isolated: 143 total Me/1000 CH$_2$; M$_w$=50,087; M$_n$=28,027; PDI=1.54.

EXAMPLES 19 AND 20

Ethylene/Methyl Acrylate Copolymerization by [5.Pd(Me)(NCMe)]BAF or [7.Pd(Me)(NCMe)]BAF Copolymerizations of ethylene and methyl acrylate catalyzed by [(ArN=C(X)—C(X)=NAr)Pd(Me)(NCMe)]BAF (0.1 mmol) were carried out at RT under 0 kPa (1 atm) of ethylene in a 40 mL CH$_2$Cl$_2$ solution which was 1.2 M in methyl acrylate. Copolymerization results for the palladium catalyst derived from ligands 5 and 7 are reported in Table 1.

TABLE 1

Ethylene (E)/methyl acrylate (MA) copolymerizations catalyzed by [(ArN=C(X)—C(X)=NAr)Pd(Me)(NCMe)]BAF.

| Ex | Ligand | TON E/MA | MA Incorp. (mol %) | M$_n$/PDI | Total Me per 1000 CH$_2$ |
|---|---|---|---|---|---|
| 19 | 5 | 97/27 | 22% | 7700/1.5 | 157 |
| 20 | 7 | 36/13 | 26% | 6700/1.8 | 233 |

EXAMPLES 21–26

General Procedure for the Synthesis of (Ligand) NiBr$_2$ Complexes

Under an inert atmosphere, a small vial was charged with 1,2-dimethoxyethane nickel dibromide (0.20 mmol to 0.30 mmol), ligand (1 equiv) and anhydrous CH$_2$Cl$_2$ (10 mL) and capped. The reaction mixture was allowed to stir for about 48 h and then filtered through a frit with Celite, rinsing well with anhydrous CH$_2$Cl$_2$. After removal of solvent under vacuum, the product was washed with anhydrous hexane, collected on a frit, transferred to a vial, and dried under vacuum.

EXAMPLE 21

Synthesis of 5.NiBr$_2$

The above general procedure was followed on a 0.20 mmol scale; yield: 56 mg (49%) pale brown powder. This compound was recrystallized from methylene chloride and a X-ray crystal structure obtained using an Enraf-Nonius CAD4 diffractometer and MoKalpha radiation. The compound had the following characteristics: monoclinic, C2/c (No. 15), a=11.648(2) Å, b=14.302(2) Å, c=13.995(4) Å, beta=104.71(2)°, T=−75° C., Vol=2255.0 Å$^3$, Z=4, Formula weight 565.01, Density 1.664 g/cc, $\mu$(Mo)=43.90 cm$^{-1}$. The crystal structure indicated that this ligand was a bidentate ligand to the nickel atom coordinated with the imino nitrogen atoms.

EXAMPLE 22

Synthesis of 6.NiBr$_2$

The above general procedure was followed on a 0.20 mmol scale; yield: 76 mg (56%) mint green powder.

EXAMPLE 23

Synthesis of 8.NiBr$_2$

The above general procedure was followed on a 0.25 mmol scale; yield: 120 mg (72%) yellow solid.

EXAMPLE 24

Synthesis of 11.NiBr$_2$

The above general procedure was followed on a 0.25 mmol scale; yield: 173 mg mint green solid.

EXAMPLE 25

Synthesis of 12.NiBr$_2$

The above general procedure was followed on a 0.25 mmol scale; yield: 179 mg mint green solid.

EXAMPLE 26

Synthesis of 13.NiBr$_2$

The above general procedure was followed on a 0.20 mmol scale; yield: 126 mg pale green solid.

EXAMPLE 27–32

Ethylene Polymerizations with Ligand.NiBr$_2$ Complexes

In a drybox, a thick-walled Schlenk flask was charged with the ligand.NiBr$_2$ complex, 20 mL of toluene and a stir bar. The vessel was sealed and transferred to a Schlenk line in the hood and purged first with nitrogen and then with ethylene. Polymethylaluminoxane/toluene (PMAO) (9.5% Al, 1.4 mmol Al) was then quickly added and the reaction mixture was stirred under 28–35 kPa of ethylene for 19.5 h. The reaction mixture was quenched with 15 mL of 90/10 methanol/HCl. The polymer was collected on a frit, rinsed with methanol and acetone and then dried overnight. The polymer was submitted for the following analyses: $^1$H NMR, GPC and DSC.

TABLE 2

Ethylene polymerization screening with MAO activation of ligand NiBr$_2$.

| Ex | Ligand | Yield PE | DSC/$^1$H NMR | GPC |
|---|---|---|---|---|
| 27 | 5 | 0.523 g 311 TO | $T_m$ = 86.3° C. $\Delta H_f$ = 21.71 J/g NMR: insoluble | $M_w$ = 806,122 $M_n$ = 192,786 |
| 28 | 6 | 2.630 g 1560 TO | $T_g$ = −65.45° C. NMR: 181.1 Me/1000 CH$_2$ | $M_w$ = 73,519 $M_n$ = 39,317 |
| 29 | 8 | 0.819 g 487 TO | $T_g$ = −94.05° C. $T_m$ = 104.84° C. $\Delta H_f$ = 46.65 J/g | $M_w$ = 637,232 $M_n$ = 222,280 |
| 30 | 11 | 0.678 g 403 TO | $T_g$ = −75, −30° C. $T_m$ = 105, 120° C. $\Delta H_f$ = 4.6, 0.94 J/g | $M_w$ = 931,625 $M_n$ = 491,427 |
| 31 | 12 | 0.551 g 327 TO | $T_g$ = −101.05° C. $T_m$ = 102.58° C. $\Delta H_f$ = 90.56 J/g | $M_w$ = 627,620 $M_n$ = 111,466 |
| 32 | 13 | 0.431 g 260 TO | $T_m$ = 104.80° C. $\Delta H_f$ = 18.79 J/g NMR: insoluble | $M_w$ = 878,578 $M_n$ = 243,875 |

EXAMPLE 33

A mixture of 0.075 g (0.21 mmol) 7 and 0.060 g (0.19 mmol) nickel dibromide-dimethoxyethane complex in 3 mL methylene chloride was stirred at RT under nitrogen for 20 h and then was rotovapped to dryness, yielding 0.115 g (98%) of the NiBr$_2$ complex of 7 as a tan powder.

A 600-mL Parr® autoclave (connected to a 1 L ethylene reservoir tank) was loaded with 200 mL dry hexane (dried over silica-supported MAO). The solvent was stirred and saturated with ethylene at 60° C. and 200 kPag. The autoclave was vented and a red solution of 2.0 mg (0.0034 mmol) of the above complex and 1 mL modified methylaluminoxane (Akzo MMAO-3A; nominal 1.7M in heptane; contains about 30% isobutyl groups) in 3 mL toluene (complex and MMAO were mixed about 1 min before injection) was taken up into a 5-mL syringe and was quickly injected into the autoclave through a head port. The autoclave was immediately pressured to 1.03 MPag with ethylene and was stirred in a 60° C. water bath for 1 h as ethylene was fed and the 1-L ethylene reservoir tank pressure drop was monitored with time (see data below). The ethylene was then vented and the clear solution was diluted with acetone to precipitate the gummy polymer; oven-drying (70° C./nitrogen) yielded 2.37 g (24,600 TO/hr; 11.8 kg PE/g Ni) clear, rubbery polyethylene. $^1$H NMR (CDCl$_2$CDCl$_2$; 120° C.): 173 CH$_3$/1000 CH$_2$. GPC (TCB; 135° C.; PE standard): Mn=46,000; Mw=103,000; Mz=164,000; Mw/Mn=2.23; Mp=92,100. $^{13}$C NMR: total Me (179.0); Me (125.1); Et (18.0); Pr (5.4); Bu (9.4); Am (3.3); Hex+ and EOC (17.4).

Ethylene tank pressure drop vs polymerization time (1-L tank)

| Time, min | E Tank, MPa | E Tank MPa |
|---|---|---|
| 0.00 | 3.67 | 4.74 |
| 1.00 | 3.63 | 4.67 |
| 4.00 | 3.61 | 4.64 |
| 10.0 | 3.60 | 4.62 |
| 15.00 | 3.58 | 4.60 |
| 30.00 | 3.56 | 4.56 |
| 60.00 | 3.53 | 4.51 |

What is claimed is:

1. A compound of the formula (IV)

$$\begin{array}{c} R^4 \quad R^5 \quad R^6 \quad R^7 \\ \diagdown \diagup \quad \diagdown \diagup \\ A \quad\quad\quad E \\ \diagdown \quad\quad \diagup \\ R^3 - N \quad\quad N - R^8 \\ \diagdown M \diagup \\ X_n \end{array}$$

$[Ar^1HNC(O)OR^9]MX_n$, or (V)

$[Ar^1HNC(O)NHR^{10}]MX_n$, (VI)

wherein:

M is Ni, Pd, Ti, Zr, Sc, V, Cr, Fe, Co or a rare earth metal;

each X is independently a monoanion;

n is equal to the oxidation number of M;

A and E are each independently oxygen, sulfur, phosphorous, or nitrogen;

$R^3$ and $R^8$ are each independently hydrocarbyl or substituted hydrocarbyl provided that the carbon atom bound to the nitrogen atom is bound to at least two other carbon atoms;

$R^4$, $R^5$, $R^6$ and $R^7$ are each independently hydrocarbyl or substituted hydrocarbyl;

$Ar^1$ and $Ar^2$ are each independently aryl or substituted aryl;

$R^9$ and $R^{10}$ are each independently hydrocarbyl or substituted hydrocarbyl;

and provided that
 when said compound is (V) or (VI), M is Ni;
 the members of any one or more of the pairs $R^4$ and $R^5$, $R^6$ and $R^7$, $R^4$ and $R^6$, and $R^5$ and $R^7$ taken together may form a ring;
 when A is oxygen or sulfur, $R^5$ is not present; and
 when E is oxygen or sulfur, $R^7$ is not present.

2. The compound as recited in claim 1 wherein A is nitrogen or phosphorous, and $R^4$ and $R^5$ taken together form a ring.

3. The compound as recited in claim 1 or 2 wherein M is Ni.

4. The compound as recited in claim 1 or 2 wherein M is Ti, Zr, Sc, V, Cr or a rare earth metal.

5. A compound of the formula

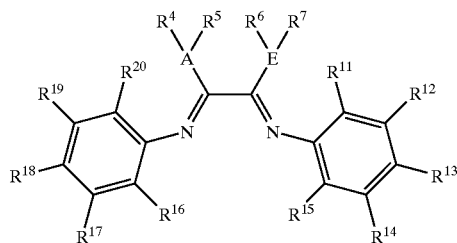

(VII)

wherein:

A and E are each independently oxygen, sulfur, phosphorous, or nitrogen;

$R^4$, $R^5$, $R^6$ and $R^7$ are each independently hydrocarbyl or substituted hydrocarbyl;

$R^{11}$ is hydrocarbyl or substituted hydrocarbyl containing 2 or more carbon atoms, or a functional group;

$R^{12}$, $R^{13}$, $R^{14}$, $R^{15}$, $R^{16}$, $R^{17}$, $R_{18}$, $R^{19}$, and $R^{20}$ are each independently hydrogen, hydrocarbyl, substituted hydrocarbyl or a functional group;

and provided that the members of any one or more of the pairs $R^4$ and $R^5$, $R^6$ and $R^7$, $R^4$ and $R^6$, and $R^5$ and $R^7$ taken together may form a ring;

any two of $R^{11}$, $R^{12}$, $R^{13}$, $R^{14}$, $R^{15}$, $R^{16}$, $R^{17}$, $R^{18}$, $R^{19}$, and $R^{20}$ vicinal to one another taken together may form a ring with the further proviso that if $R^{11}$ and $R^{12}$ are taken together to form a ring, then $R^{11}$ and $R^{12}$ taken together contain at least 2 carbon atoms;

when A is oxygen or sulfur, $R^5$ is not present; and when E is oxygen or sulfur, $R^7$ is not present.

6. The compound as recited in claim 5 wherein A is nitrogen or phosphorous, and $R^4$ and $R^5$ taken together form a ring.

7. The compound as recited in claim 1 or 5 wherein both A and E are nitrogen.

8. The compound as recited in claim 1 or 5 wherein A and E taken together are part of a ring.

* * * * *